United States Patent
Kenney

(10) Patent No.: US 10,885,762 B1
(45) Date of Patent: Jan. 5, 2021

(54) MOLD ALERT ASSEMBLY

(71) Applicant: Kathleen Kenney, Baltimore, MD (US)

(72) Inventor: Kathleen Kenney, Baltimore, MD (US)

( * ) Notice: Subject to any disclaimer, the term of this patent is extended or adjusted under 35 U.S.C. 154(b) by 0 days.

(21) Appl. No.: 16/796,466

(22) Filed: Feb. 20, 2020

(51) Int. Cl.
| | | |
|---|---|---|
| *G08B 21/00* | (2006.01) | |
| *G08B 21/12* | (2006.01) | |
| *G08B 7/06* | (2006.01) | |
| *C12Q 1/04* | (2006.01) | |
| *G08B 3/10* | (2006.01) | |
| *G08B 5/36* | (2006.01) | |

(52) U.S. Cl.
CPC ............... *G08B 21/12* (2013.01); *C12Q 1/04* (2013.01); *G08B 7/06* (2013.01); *G08B 3/10* (2013.01); *G08B 5/36* (2013.01)

(58) Field of Classification Search
CPC ........ G08B 21/12; G08B 21/20; G01N 25/58; G01N 17/00; G01N 27/223; G01N 19/10
See application file for complete search history.

(56) References Cited

U.S. PATENT DOCUMENTS

| | | |
|---|---|---|
| 6,798,220 B1 | 9/2004 | Flanigan |
| 7,334,938 B2 | 2/2008 | Remsburg |
| 7,382,269 B2 | 6/2008 | Remsburg |
| 8,707,762 B2 * | 4/2014 | Pfanstiehl ............ G01M 3/047 73/29.04 |
| 8,726,721 B2 | 5/2014 | Minges |
| D741,204 S | 10/2015 | Chen |
| 2007/0026107 A1 | 2/2007 | Wang |
| 2008/0070244 A1 | 3/2008 | Gartner |
| 2013/0133404 A1 * | 5/2013 | Patel ........................ F24F 11/30 73/29.02 |

FOREIGN PATENT DOCUMENTS

WO    WO2007130522    11/2007

* cited by examiner

*Primary Examiner* — Toan N Pham

(57) ABSTRACT

A mold alert assembly for alerting a user to the presence of mold spores includes a housing that is mountable within a building. The housing has a plurality of vents each extending into an interior of the housing. A mold detection unit is positioned within the housing and the mold detection unit is in fluid communication with the vents to sample ambient air. The mold detection unit is actuated to emit an alert when the mold detection unit detects mold. In this way the mold detection unit can alert a user to the presence of mold.

9 Claims, 4 Drawing Sheets

MOLD ALERT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to mold alert devices and more particularly pertains to a new mold alert device for alerting a user to the presence of mold spores.

(2) Description of Related Art Including Information Disclosed Under 37 CFR 1.97 and 1.98

The prior art relates to mold alert devices. The prior art discloses a moisture sensor for sensing moisture behind drywall for detecting mold. The prior art discloses a variety of means of sampling environmental conditions for identifying areas that could potentially foster mold growth. A variety of algorithms are used for determining the probability of mold growth in each respective environment based on the sampled environmental conditions.

BRIEF SUMMARY OF THE INVENTION

An embodiment of the disclosure meets the needs presented above by generally comprising a housing that is mountable within a building. The housing has a plurality of vents each extending into an interior of the housing. A mold detection unit is positioned within the housing and the mold detection unit is in fluid communication with the vents to sample ambient air. The mold detection unit is actuated to emit an alert when the mold detection unit detects mold. In this way the mold detection unit can alert a user to the presence of mold.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
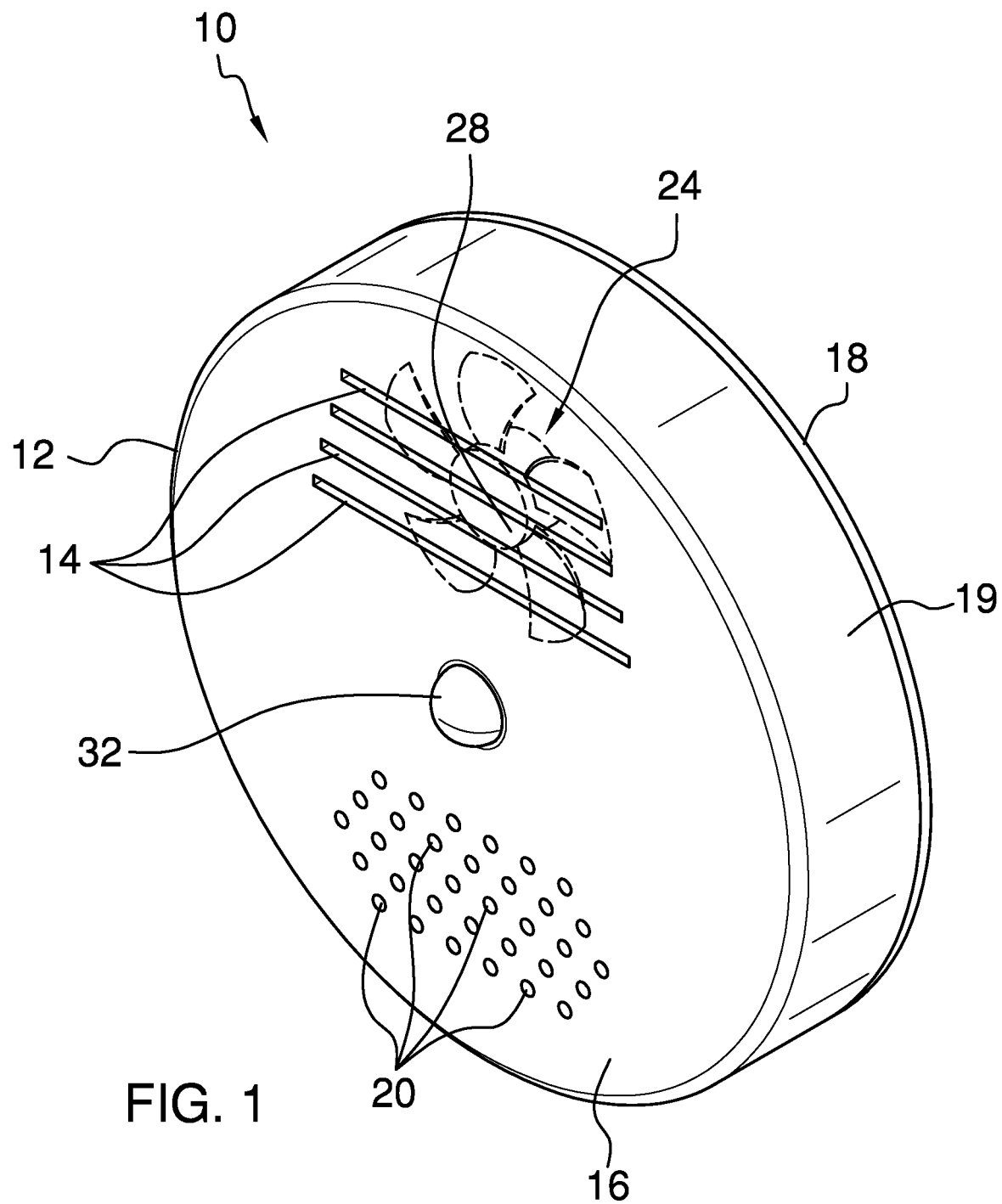
FIG. 1 is a perspective phantom view of a mold alert assembly according to an embodiment of the disclosure.
Figure 2:
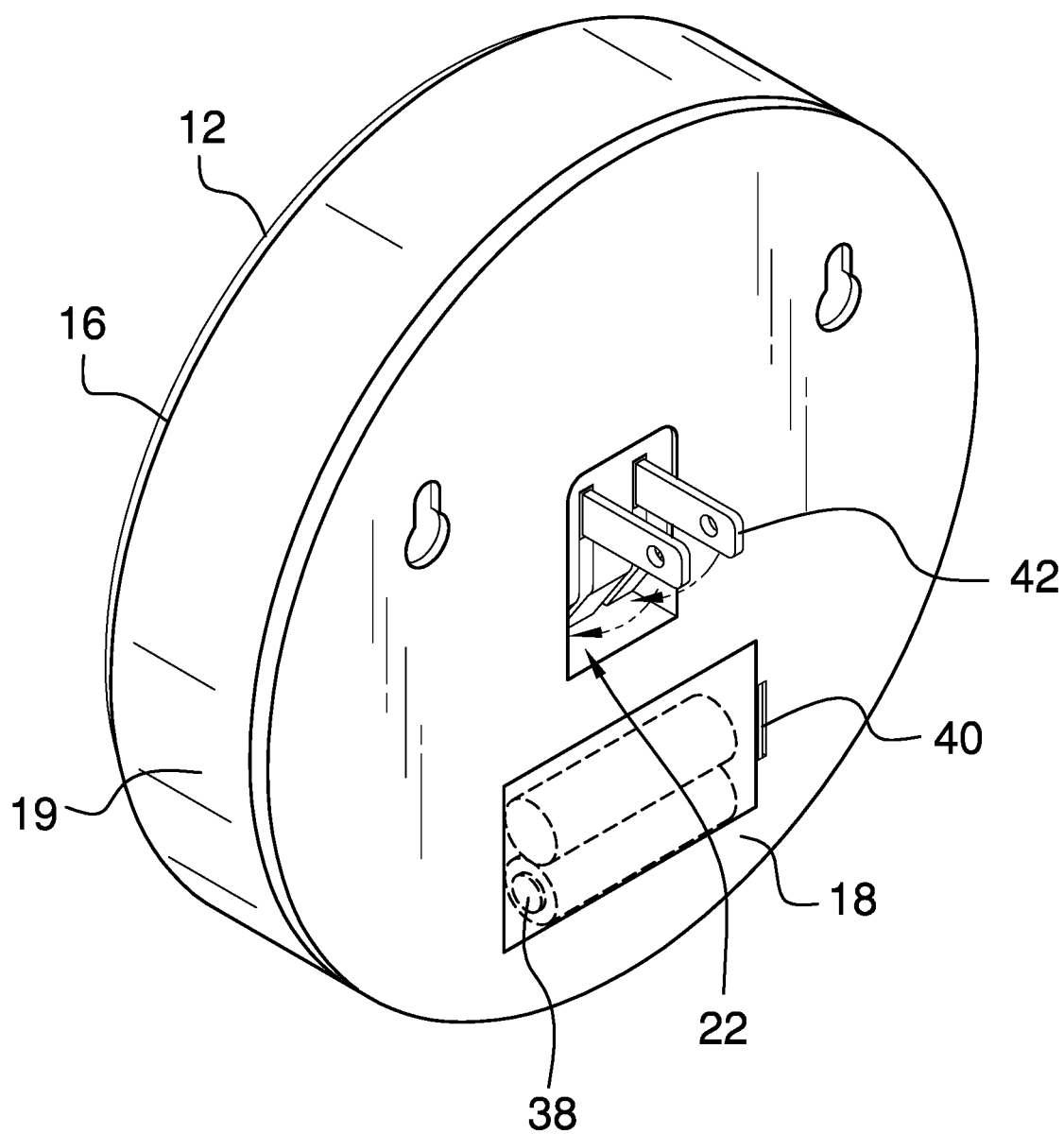
FIG. 2 is a back perspective view of an embodiment of the disclosure.
Figure 3:
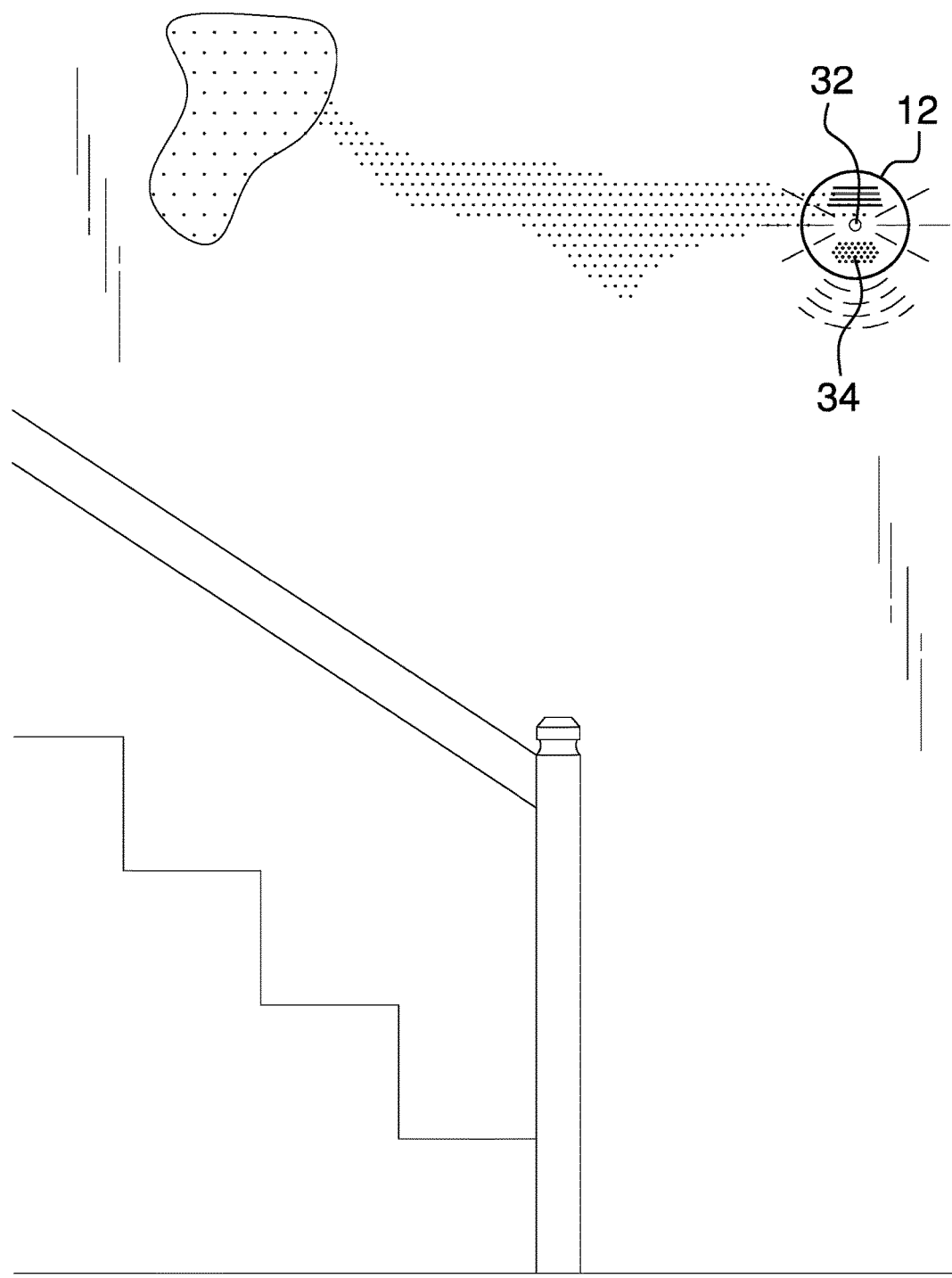
FIG. 3 is a perspective in-use view of an embodiment of the disclosure.
Figure 4:
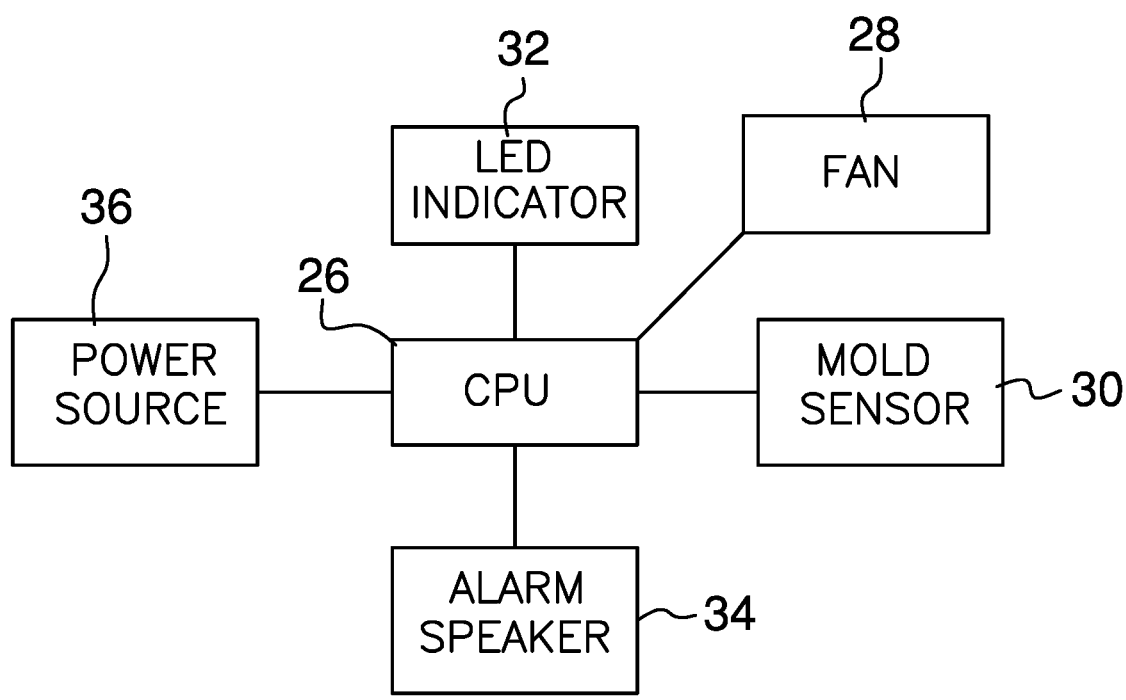
FIG. 4 is a schematic view of an embodiment of the disclosure.

With reference now to the drawings, and in particular to FIGS. 1 through 4 thereof, a new mold alert device embodying the principles and concepts of an embodiment of the disclosure and generally designated by the reference numeral 10 will be described.

As best illustrated in FIGS. 1 through 4, the mold alert assembly 10 generally comprises a housing 12 that is mountable within a building. The building may be a house, a business or any other type of dwelling. The housing 12 has a plurality of vents 14 each extending into an interior of the housing 12. The housing 12 has a front wall 16, a back wall 18 and a perimeter wall 19 extending therebetween. The perimeter wall 19 is continuously arcuate about a center point of the housing 12 such that the housing 12 has a puck shape. Each of the vents 14 extends through the front wall 16, and the front wall 16 has a plurality of speaker openings 20 each extending into the interior of the housing 12. The back wall 18 has a recess 22 extending inwardly therein and the back wall 18 is attached to a support surface in the building.

A mold detection unit 24 is positioned within the housing 12. The mold detection unit 24 is in fluid communication with the vents 14 to sample ambient air. Additionally, the mold detection unit 24 is actuated to emit an alert when the mold detection unit 24 detects mold. In this way the mold detection unit 24 can alert a user to the presence of mold. The mold detection unit 24 comprises a control circuit 26 that is positioned within the housing 12 and the control circuit 26 receives an alert input. A fan 28 is rotatably positioned within the housing 12 and the fan 28 is electrically coupled to the control circuit 26. The fan 28 is aligned with the vents 14 in the housing 12 to draw air inwardly through the vents 14 when the fan 28 is turned on. Additionally, the fan 28 is cycled on and off at pre-determined intervals of time.

A mold sensor 30 is positioned within the housing 12 and the mold sensor 30 is electrically coupled to the control circuit 26. The mold sensor 30 is in fluid communication with the fan 28 thereby facilitating the mold sensor 30 to be exposed to ambient air urged by the fan 28. In this way the mold sensor 30 tests the ambient air for mold spores. The control circuit 26 receives the alert input when the mold sensor 30 senses mold spores in a concentration that exceeds a predetermined, minimum concentration. The mold sensor 30 may comprise an electronic mold sensor that is capable of sensing mold spores, including but not being limited to black mold spores, known to cause allergic reactions in people.

A light emitter 32 is coupled to the front wall 16 of the housing 12 to emit light outwardly therefrom. The light emitter 32 is electrically coupled to the control circuit 26 and the light emitter 32 is turned on when the control circuit 26 receives the alert input. In this way the light emitter 32 can visually alert a user to the presence of mold spores. A speaker 34 is positioned within the housing 12 for emitting an audible alert. The speaker 34 is electrically coupled to the control circuit 26 and the speaker 34 is aligned with the speaker openings 20. The speaker 34 is turned on when the control circuit 26 receives the alert input to audibly alert the user to the presence of mold spores. The speaker 34 may be an electronic speaker or the like.

A power supply 36 is coupled to the housing 12 and the power supply 36 is electrically coupled to the control circuit 26. The power supply 36 comprises at least one battery 38 that is positioned in the housing 12 and the at least one battery 38 is electrically coupled to the control circuit 26. A battery cover 40 is removably coupled to the back wall 18 of the housing 12 and the at least one battery 38 is positioned beneath the battery cover 40.

The power supply 36 includes a male electrical plug 42 that is movably coupled to the back wall 18 and which is also positioned in the recess 22. The male electrical plug 42 is positionable in a deployed position for plugging the male electrical plug 42 into a female electrical outlet. Additionally, the male electrical plug 42 is pivotable into a stored position having the male electrical plug 42 being stored in the recess 22.

In use, the housing 12 is mounted at a location in the building that is well exposed to ambient air. The fan 28 is cycled on and off to repeatedly draw ambient air across the mold sensor 30. In this way the mold sensor 30 can test the ambient air for mold spores. The light emitter 32 and the speaker 34 are both turned on when the mold sensor 30 senses mold spores. In this way the user is alerted to the presence of mold and can subsequently take appropriate action. Thus, the user can avoid a potentially life threatening allergic reaction.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A mold alert assembly being configured to continuously sample ambient air and emit an alert when mold is detected, said assembly comprising:
   a housing being mountable within a building, said housing having a plurality of vents each extending into an interior of said housing; and
   a mold detection unit being positioned within said housing, said mold detection unit being in fluid communication with said vents wherein said mold detection unit is configured to sample ambient air, said mold detection unit being actuated to emit an alert when said mold detection unit detects mold wherein said mold detection unit is configured to alert a user to the presence of mold.

2. The assembly according to claim 1, wherein said housing has a front wall and a back wall, each of said vents extending through said front wall, said front wall having a plurality of speaker openings each extending into said interior of said housing, said back wall having a recess extending inwardly therein, said back wall being attached to a support surface in the building.

3. The assembly according to claim 2, wherein said mold detection unit comprises a control circuit being positioned within said housing, said control circuit receiving an alert input.

4. The assembly according to claim 3, wherein said mold detection unit includes a fan being rotatably positioned within said housing, said fan being electrically coupled to said control circuit, said fan being aligned with said vents in said housing wherein said fan is configured to draw air inwardly through said vents when said fan is turned on, said fan being cycled on and off at pre-determined intervals of time.

5. The assembly according to claim 4, wherein said mold detection unit includes a mold sensor being positioned within said housing, said mold sensor being electrically coupled to said control circuit, said mold sensor being in fluid communication with said fan thereby facilitating said mold sensor to be exposed to ambient air urged by said fan wherein said mold sensor is configured to test the ambient air for mold spores, said control circuit receiving said alert input when said mold sensor senses mold spores.

6. The assembly according to claim 3, wherein said mold detection unit includes a light emitter being coupled to said front wall of said housing wherein said light emitter is configured to emit light outwardly therefrom, said light emitter being electrically coupled to said control circuit, said light emitter being turned on when said control circuit receives said alert input wherein said light emitter is configured to visually alert the user to the presence of mold spores.

7. The assembly according to claim 3, wherein said mold detection unit includes a speaker being positioned within said housing wherein said speaker is configured to emit an audible alert, said speaker being electrically coupled to said control circuit, said speaker being aligned with said speaker openings, said speaker being turned on when said control circuit receives said alert input wherein said speaker is configure to audibly alert the user to the presence of mold spores.

8. The assembly according to claim 3, wherein said mold detection unit includes a power supply being coupled to said housing, said power supply being electrically coupled to said control circuit, said power supply comprising:
- at least one battery being positioned in said housing, said at least one battery being electrically coupled to said control circuit;
- a battery cover being removably coupled to said back wall of said housing, said at least one battery being positioned beneath said battery cover; and
- a male electrical plug being movably coupled to said back wall, said male electrical plug being positioned in said recess, said male electrical plug being positionable in a deployed position for plugging said male electrical plug into a female electrical outlet, said male electrical plug being pivotable into a stored position having said male electrical plug being stored in said recess.

9. A mold alert assembly being configured to continuously sample ambient air and emit an alert when mold is detected, said assembly comprising:

- a housing being mountable within a building, said housing having a plurality of vents each extending into an interior of said housing, said housing having a front wall and a back wall, each of said vents extending through said front wall, said front wall having a plurality of speaker openings each extending into said interior of said housing, said back wall having a recess extending inwardly therein, said back wall being attached to a support surface in the building; and
- a mold detection unit being positioned within said housing, said mold detection unit being in fluid communication with said vents wherein said mold detection unit is configured to sample ambient air, said mold detection unit being actuated to emit an alert when said mold detection unit detects mold wherein said mold detection unit is configured to alert a user to the presence of mold, said mold detection unit comprising: a control circuit being positioned within said housing, said control circuit receiving an alert input;
- a fan being rotatably positioned within said housing, said fan being electrically coupled to said control circuit, said fan being aligned with said vents in said housing wherein said fan is configured to draw air inwardly through said vents when said fan is turned on, said fan being cycled on and off at pre-determined intervals of time;
- a mold sensor being positioned within said housing, said mold sensor being electrically coupled to said control circuit, said mold sensor being in fluid communication with said fan thereby facilitating said mold sensor to be exposed to ambient air urged by said fan wherein said mold sensor is configured to test the ambient air for mold spores, said control circuit receiving said alert input when said mold sensor senses mold spores;
- a light emitter being coupled to said front wall of said housing wherein said light emitter is configured to emit light outwardly therefrom, said light emitter being electrically coupled to said control circuit, said light emitter being turned on when said control circuit receives said alert input wherein said light emitter is configured to visually alert the user to the presence of mold spores;
- a speaker being positioned within said housing wherein said speaker is configured to emit an audible alert, said speaker being electrically coupled to said control circuit, said speaker being aligned with said speaker openings, said speaker being turned on when said control circuit receives said alert input wherein said speaker is configure to audibly alert the user to the presence of mold spores; and
- a power supply being coupled to said housing, said power supply being electrically coupled to said control circuit, said power supply comprising:
- at least one battery being positioned in said housing, said at least one battery being electrically coupled to said control circuit; a battery cover being removably coupled to said back wall of said housing, said at least one battery being positioned beneath said battery cover; and a male electrical plug being movably coupled to said back wall, said male electrical plug being positioned in said recess, said male electrical plug being positionable in a deployed position for plugging said male electrical plug into a female electrical outlet, said male electrical plug being pivotable into a stored position having said male electrical plug being stored in said recess.

* * * * *